(12) United States Patent
Elsbrock et al.

(10) Patent No.: US 9,089,493 B2
(45) Date of Patent: Jul. 28, 2015

(54) SKIN CARE COMPOSITION

(75) Inventors: Robert John Elsbrock, Cincinnati, OH (US); Paul Robert Tanner, Lebanon, OH (US); Juliet Ann Jones, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 2430 days.

(21) Appl. No.: 11/228,766

(22) Filed: Sep. 16, 2005

(65) Prior Publication Data
US 2007/0065381 A1    Mar. 22, 2007

(51) Int. Cl.
| A61Q 19/00 | (2006.01) |
| A61K 8/29 | (2006.01) |
| A61K 8/19 | (2006.01) |
| A61K 8/11 | (2006.01) |
| A61K 8/64 | (2006.01) |
| A61K 8/891 | (2006.01) |
| A61K 8/894 | (2006.01) |

(52) U.S. Cl.
CPC ... *A61K 8/29* (2013.01); *A61K 8/11* (2013.01); *A61K 8/19* (2013.01); *A61K 8/64* (2013.01); *A61K 8/891* (2013.01); *A61K 8/894* (2013.01); *A61Q 19/00* (2013.01); *A61K 2800/412* (2013.01); *A61K 2800/436* (2013.01)

(58) Field of Classification Search
CPC ............ A61K 8/11; A61K 8/29; A61K 8/19; A61Q 19/00
USPC ......................................... 106/481; 424/401
See application file for complete search history.

(56) References Cited

U.S. PATENT DOCUMENTS

| 5,008,143 A * | 4/1991 | Armanini ...................... 428/207 |
| 5,116,664 A | 5/1992 | Kimura et al. |
| 5,223,559 A | 6/1993 | Arraudeau et al. |
| 5,587,168 A | 12/1996 | Vanonou |
| 5,690,916 A | 11/1997 | Kimura et al. |
| 5,932,251 A | 8/1999 | Kirkpatrick |
| 5,939,082 A | 8/1999 | Oblong |
| 5,968,528 A | 10/1999 | Deckner |
| 5,972,359 A | 10/1999 | Sine et al. |
| 6,187,298 B1 | 2/2001 | Kurz et al. |
| 6,306,409 B1 | 10/2001 | Ogawa et al. |
| 6,451,294 B1 | 9/2002 | Simon |
| 6,455,055 B1 * | 9/2002 | Walling et al. ................ 424/401 |
| 6,511,672 B2 | 1/2003 | Tan et al. |
| 2003/0003064 A1 | 1/2003 | Kalla et al. |
| 2003/0157041 A1 | 8/2003 | Dreher |
| 2004/0191198 A1 * | 9/2004 | Hochstein et al. .............. 424/63 |
| 2004/0223929 A1 | 11/2004 | Clapp et al. |
| 2004/0223991 A1 | 11/2004 | Wei et al. |
| 2004/0223993 A1 | 11/2004 | Clapp et al. |
| 2004/0234565 A1 | 11/2004 | Stella et al. |
| 2005/0220739 A1 | 10/2005 | Dreher et al. |
| 2006/0032404 A1 * | 2/2006 | Kniess .......................... 106/481 |
| 2006/0051304 A1 | 3/2006 | Peng |

FOREIGN PATENT DOCUMENTS

| JP | 08188723 | 7/1996 |
| JP | 2000-226307 | 8/2000 |
| WO | WO 00/51551 | 9/2000 |

OTHER PUBLICATIONS

Shiseido, "Graphite Pigment", Feb. 1, 1983, JP 58017171 A. abstract.*
PCT International Search Report, dated mailed: Jun. 18, 2007, 4 pages.
USPTO Office Action rejections/objections from co-pending U.S. Appl. No. 10/840,832, filed May 7, 2004; Inventor: Teresa Barbara Crook et al., mail dates Dec. 17, 2007, Jul. 9, 2008, Nov. 23, 2009, and Feb. 5, 2009 ; 31 pages.
Emmert, Dr. Ralf, "Quantification of the Soft-Focus Effect", Cosmetics & Toiletries, vol. 111, pp. 57-61 (Jul. 1996).
Flick, E. Cosmetics Additives, 1991 Noyes Publications p. 489.

* cited by examiner

*Primary Examiner* — Gina Justice
(74) *Attorney, Agent, or Firm* — S. Robert Chuey

(57) ABSTRACT

Skin care composition comprising a plurality of interference pigments and a dermatologically acceptable carrier. The plurality comprises at least a first interference pigment which reflects a first color, and at least a second interference pigment which reflects a second, complementary color. The total amount of interference pigments is from about 0.1% to about 10%.

14 Claims, 2 Drawing Sheets

SKIN CARE COMPOSITION

FIELD OF THE INVENTION

The present invention relates to a skin care composition useful for improving the appearance of visible discontinuities in mammalian skin and for improving the condition of mammalian skin.

BACKGROUND OF THE INVENTION

A variety of products are available to consumers that aid in providing a more uniform appearance to the skin and to other keratinous tissue. One way to accomplish this is through the use of compositions comprising colored pigments. For example, cosmetic foundations containing colored pigments can closely imitate the skin's natural color. One drawback of such compositions, however, is that to provide better coverage, increased amounts of pigments are required. This may result in an artificial, or "mask-like," appearance. Another drawback is that the compositions may be highly colored, and thus unsuitable for certain applications. For example, consumers tend to prefer lotions and moisturizers that are either white or relatively uncolored. In addition, the skin may exhibit many types of discoloration, for example brown age spots and/or redness due to dry skin or rosacea. It would be advantageous to be able to apply a single composition that can improve the appearance of a variety of visible discontinuities. There exists a need, therefore, for a skin care composition that has minimal color, and that can improve the appearance of a variety of visible discontinuities in skin, while maintaining a more natural appearance.

Interference pigments long have been used in personal care compositions, and provide an alternative to colored pigments for diminishing the appearance of imperfections. Interference pigments typically are thin, plate-like particles, comprising two or more layers of controlled thickness. The layers have different refractive indices, and reflect a color resulting from the constructive or destructive interference of reflections of light from the different layers. The color may be determined by selecting an appropriate thickness of the layers. Thus, in contrast to colored pigments, interference pigments are themselves colorless, yet reflect a desired color. The same interference pigment also transmits a color complementary to that which is reflected. For example, blue interference pigments reflect a blue color, yet transmit to the skin a complementary yellow color. Compositions comprising such pigments may appear blue in color when applied to the skin, which consumers may find undesirable for many applications. In addition, the applied composition would transmit a yellow color, which may be ineffective in improving the appearance of certain types of discoloration. Therefore, whereas interference pigments may be suitable to address certain skin care issues, their use as described to date fails to fulfill the needs identified herein.

SUMMARY OF THE INVENTION

Applicants have found that a composition comprising a pair of interference pigments that reflect complementary colors effectively meets the aforementioned needs. By adjusting the ratio of the first to the second interference pigment, appropriate amounts of complementary colors are combined to produce a product that appears essentially uncolored when applied to the skin, and that improves the appearance of visible discontinuities such as discoloration. Rather than comprising one type of interference pigment that appears colored when applied to the skin, the combination of interference pigments reflects colors complementary to each other. Use of complementary interference pigments in this manner is contrary to the teaching of technical publications and current practice in the art, which specifies that different colors of interference pigments should not be used in a given composition, so as to avoid possible interference with (and thus cancellation) of the desired reflected color.

Due in part to the optical properties of the interference pigments, the bulk compositions also may be substantially colorless in appearance, and thus suitable for use in a variety of skin care compositions, including, but not limited to, moisturizers and lotions. Further, without being limited by theory, Applicants believe that when the composition is applied to the skin, the interference pigments become more aligned relative to each other and the effect of the complementary pigments becomes more apparent. The reflected complementary colors may combine to produce a shade of white, which reduces the appearance of a variety of discolorations. This results in a more uniform appearance of the skin, without the unnatural, mask-like appearance that often results from application of pigmented cosmetic compositions. Thus, the use of a complementary pair of interference pigments can result in bulk compositions that are substantially colorless, and that improve the appearance of the skin without imparting significant non-white color to the skin.

The effect of the interference pigments on the skin can be modeled by spreading, or "drawing," a thin layer of the composition on a black and/or a white background. In particular, a black background makes the effect of the reflected colors more apparent, and provides information that is useful in determining an optimal ratio of interference pigments. For example, after drawing a composition onto a surface, the chroma and the contrast ratio of the composition can be measured, which characterize the color (for example, shade and intensity) and the opacity of the composition.

According to the first embodiment of the present invention, a skin care composition is provided, comprising a plurality of interference pigments, wherein said plurality comprises at least a first interference pigment which reflects a first color, and at least a second interference pigment which reflects a second, complementary color. The total amount of interference pigments comprises from about 0.1% to about 10%.

According to yet another embodiment of the present invention, a skin care composition is provided comprising a plurality of interference pigments, wherein said plurality comprises at least a first interference pigment reflecting a first color, a second interference pigment reflecting a second color, a third interference pigment reflecting a third color, and a dermatologically acceptable carrier. The chroma of the composition drawn on a black surface is from about 0 to about 6, and the total amount of interference pigments is from about 0.1% to about 10%.

Yet another embodiment of the present invention provides for a skin care composition according to either of the preceding embodiments, wherein said composition further comprises one or more skin care actives.

Yet another embodiment of the present invention provides a method for improving the appearance of visible discontinuities of skin, comprising the step of applying a composition described in any of the preceding embodiments.

Yet another embodiment of the present invention provides a method for improving the condition of mammalian skin, comprising the step of applying a composition described in any of the preceding embodiments.

Yet another embodiment provides for a kit, said kit comprising at least one composition as described herein. Optionally, the kit may comprise one or more additional compositions and/or one or more dietary supplements.

DETAILED DESCRIPTION OF THE INVENTION

Figure 1:
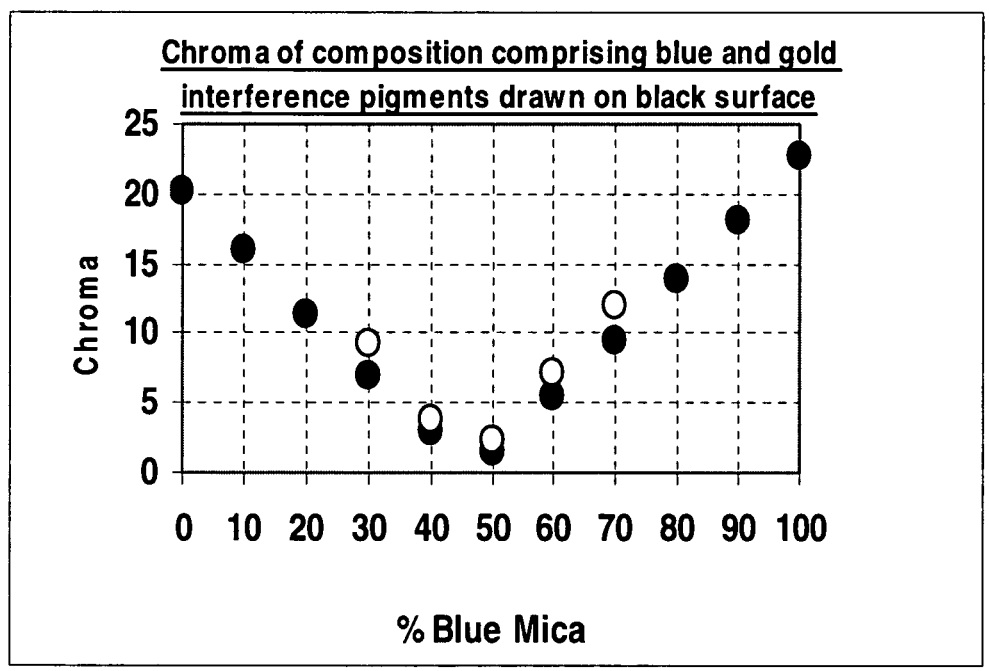
FIG. 1 depicts a graph of the chroma (y-axis) of individual compositions drawn on a black surface versus the percentage of blue interference pigment in the composition comprising a mixture of blue and gold interference pigments (x-axis).

Whereas the specification concludes with claims that particularly point out and distinctly claim the present invention, it is believed that the invention will be better understood from the following details.

The present invention describes a skin care composition useful for improving the appearance of visible discontinuities in mammalian skin and for improving the condition of mammalian skin. The composition comprises a plurality of interference pigments, wherein the plurality comprises at least a first interference pigment reflecting a first color, and a second interference pigment reflecting a second, complementary color. The ratio of the first to the second interference pigment is such that the combination of complementary colors produces a substantially colorless composition when drawn on an appropriate background as described herein. The composition may be used in a variety of skin care products, non-limiting examples of which include moisturizers, conditioners, cleansers, cosmetics, sunscreens, anti-aging compounds, and combinations thereof. In one embodiment, the composition is applied to the face, neck and other exposed areas of the body.

In all embodiments of the present invention, all percentages are by weight of the total composition, unless specifically stated otherwise. All ratios are weight ratios, unless specifically stated otherwise. The number of significant digits conveys neither limitations on the indicated amounts nor on the accuracy of the measurements. All amounts indicating quantities, percentages, proportions, etc. are understood to be modified by the word "about" unless otherwise specifically indicated. All measurements are understood to be made at about 25° C. and at ambient conditions, where "ambient conditions" means conditions under about one atmosphere of pressure and at about 50% relative humidity.

Herein, "skin care composition" means a composition suitable for topical application on mammalian skin. Herein, "topical application," as used herein, means to apply or spread a composition onto the surface of the skin. The skin care composition described herein may contain one or more skin care actives. "Skin care actives," or "actives," as used herein, means compounds that, when applied to the skin provide a benefit and/or improvement to the skin.

Herein, "dermatologically-acceptable," means that the compositions or components thereof so described are suitable for use in contact with mammalian skin without undue toxicity, incompatibility, instability, allergic response, and the like.

Herein, "improving the appearance of visible discontinuities" means improving the appearance of mammalian skin such that a positive change in skin appearance after topically applying the composition of the present invention is observed, macroscopically (without visual aid) and/or microscopically under magnification of 10× or 100×, relative to before topical application of the composition. "Visible discontinuities" include, but are not limited to, discoloration due to hyperpigmentation of skin, including but not limited to, age spots and freckles; and hyperchromic areas, including but not limited to, under-eye circles, blotchiness (e.g., uneven red coloration due to, for example, rosacea), sallowness, discoloration caused by telangiectasia or spider vessels, and uneven skin tone.

Herein, "improving the condition of mammalian skin" means effecting an improvement in the skin which may or may not be related to discoloration, for example, regulating signs of ageing, including wrinkles, deep and fine lines, crevices, bumps, large pores, unevenness or roughness and loss of skin elasticity.

Herein, "complementary" means two or more colors which, when combined in an appropriate ratio in an additive system, produce a minimum chroma in the absence of colorants such as dyes and/or pigments. Referring to FIG. 1, the closed circles represent compositions comprising a total amount of interference pigments of about 2%, and the open circles represent compositions comprising a total amount of interference pigments of about 5%. The compositions are substantially free of dyes and/or colorants. It is noted that a similar graph could be obtained by measuring compositions comprising any pair of complementary interference pigments, for example, green and red. Non-limiting examples of complementary colors include blue and gold (herein used interchangeably with "yellow"), and red and green.

Herein, "colorant," or equivalent terms, refers to a substance which imparts color in a subtractive (i.e. all colors combine to produce black), rather than an additive system. Examples of colorants include, but are not limited to, dyes, organic and inorganic pigments other than interference pigments, etc.

Herein, "chroma," describes color and color intensity. For the purposes of the present invention, color is defined according to a value on the CIELAB color system, which is based on the XYZ color system, defined by the Commission Internationale de l'Eclairage (CIE system) to provide a manner of objectively representing perceived color and color differences. X, Y and Z can be expressed in a variety of manners, or "scales," one of which is the Hunter scale. The Hunter scale has three variables, L, a, and b, which correlate mathematically to X, Y and Z, and is described by Robertson, A. R. in "The CIE 1976 Color Difference Formulas," *Color Research Applications*, vol. 2, pp. 7-11 (1977). The compositions of the present invention may be analyzed with a MINOLTA® CR-200 Chroma Meter, which generates values for L, a, and b. The value for "a" correlates to a value along the red-green (horizontal) axis, and the value for "b" correlates to a value along the blue-yellow (vertical) axis. For example, a blue-colored sample will have a negative b-value, whereas a red-colored sample will have a positive a-value. A more positive or negative value represents a more intense color. The value for "L" is an indicator of lightness and/or darkness, and correlates to a value along the z-axis, which is perpendicular to both the horizontal and vertical axes. "Chroma" is measured by a vector having its origin at the intersection of the red-green and blue-yellow axes and extending outward into the color space defined by the horizontal and vertical axes of the CIELAB color system. The length of the vector represents the chroma, and the direction of the vector represents the shade, or hue. The shorter the vector, the less colored is the composition, and the lower the chroma. Herein, "substantially colorless" used in reference to bulk compositions means the composition has a chroma of about 10.0 or less, and is understood herein to include white compositions.

Herein, "drawn" means that the composition is applied onto an opacity chart (Form 2A, Leneta Company of Manwah, N.J. or the equivalent thereof, of which the top half is black and the bottom half is white) and spread into a film having a thickness of approximately 0.0015 inches using a film applicator (e.g., as commercially available from BYK Gardner of Columbia, Md., or the equivalent thereof). The chroma may be measured after the film is allowed to dry for 4 hours under conditions of 22° C.+/−2° C., 1 atm. Herein, "drawn onto a black surface" means that although the product may be drawn onto both the black and the white portions of the opacity chart, the chroma is measured on the only the black portion of the chart. Herein, "substantially colorless" used in reference to a composition drawn on a black surface means that the drawn composition has a chroma of about 6.0 or less, and is understood herein to include white compositions.

Herein, "bulk" means a volume of composition, for example at least 1 cubic centimeter (ccm), which has not been spread out, or "drawn."

Herein, "hue" describes the shade of a color. Hue is measured by the angle formed between the chroma vector and the positive portion of the red-green (horizontal) axis, as the vector is rotated in a counter-clockwise direction. Thus, a hue of 0 represents a red color, a hue of 90 a yellow color, a hue of 180 a green color, and a hue of 270 a blue color.

Herein, "contrast ratio" refers to the opacity of the composition, or the ability of the composition to reduce or prevent light transmission, determined after the composition is drawn onto an opacity chart (Form 2A, Leneta Company of Manwah, N.J. or the equivalent thereof), and by using a chromameter (e.g., a Minolta CR-200 Chromameter, d65 illuminant, 0 degree viewing angle, commercially available from the Minolta Camera Co. of Ramsey, N.J. and described in the chromameter manual, version 3.0; 1988, incorporated herein by reference, or the equivalent thereof). The composition is drawn into a film having a thickness of approximately 0.0015 inches as described above. The film is allowed to dry for 4 hours under conditions of 22° C.+/−1° C., 1 atm. Using the chromameter, the Y tristimulus value (i.e., the XYZ color space of the film) of the product film is measured and recorded. The Y tristimulus value is measured in three different areas of the product film over the black section of the opacity chart, and also in three different areas of the product film over the white section of the opacity chart. The contrast ratio is calculated as the mathematical average of the three Y tristimulus values over the black areas, divided by the mathematical average of the three Y tristimulus values over the white areas, times 100:

$$\text{Contrast Ratio} = \frac{\text{average (three } Y_{black})}{\text{average (three } Y_{white})} \times 100$$

Herein, "adjusted contrast ratio" means a contrast ratio which has been calibrated by subtracting the contrast ratio of a blank opacity chart, i.e. a chart without any product applied.

Herein, "delivery enhancement device" means any device that increases the amount of composition applied to and/or into the skin, more easily and/or efficiently delivers the composition, and/or increases the beneficial results derived from the composition, relative to that delivered without using the device.

Herein, "dietary supplement" means a dietary ingredient intended to supplement a regular diet, non-limiting examples of which include vitamins, minerals, herbs or other botanicals, amino acids, enzymes and metabolites. Herein, the dietary supplement is suitable for oral consumption and is administered orally. Examples of dietary supplements suitable for use in the present invention include, but are not limited to, vitamins and vitamin derivatives, peptides, essential fatty acids, and sugar amines. The form in which the dietary supplement is administered may vary widely, and includes, for example, tablets, capsules, gel tablets, and liquids. The dietary supplement further may be incorporated into a foodstuff or beverage.

Herein "kit" means a packaging unit comprising at least one composition described herein. The kit may comprise an outer packaging unit, which in turn may comprise one or more inner packaging units. The inner and outer packaging units may be of any type suitable for containing, presenting and/or reasonably protecting from damage the contents of the kit. The kit may comprise a plurality of components, including at least one additional compositions, one or more orally ingestible dietary supplements, a delivery enhancement device, instructions for use of the device, instructions for complying with suitable application regimens, a substrate, and combinations thereof.

I. Interference Pigments

The composition of the present invention comprises interference pigments. Herein, "interference pigment" means one type of interference pigment having a characteristic reflected color. For the purposes of the present specification, interference pigments are defined as particles having two or more layers of controlled thickness with different refractive indices. The interference pigments yield a characteristic reflected color from the interference of typically two, but occasionally more, light reflections, from different layers of the particle, which may be thin and plate-like. Non-limiting examples of suitable interference pigments for the composition of the present invention comprise a base substrate particle comprised of natural or synthetic mica, borosilicate glass, silica, and mixtures thereof, layered with films of $TiO_2$, silica, tin oxide, iron oxide, and mixtures thereof, wherein the thickness of the layers is from about 50 nm to about 300 nm. In one embodiment the interference pigments are substantially colorless when viewed macroscopically in bulk powder form, and the film layer is $TiO_2$.

Useful intereference pigments are available commercially from a wide variety of suppliers, for example, Rona (Timiron™), Sensient (Covapearl™), Englehard (Flamenco™), Kobo (KTZ Interval™ and Interfine™) and Eckart (Prestige™). In one non-limiting embodiment, the interference pigments have an average diameter of individual particles in the longest direction of from about 5 microns to about 75 microns, alternatively from about 5 microns to about 25 microns, and alternatively from about 10 to about 20 microns.

Alternatively, the interference pigment may comprise an additional surface treatment to reduce interactions with other materials, to modify the skin feel, and/or to improve dispersability. For example, the surface may be hydrophobically modified to increase suspension in a hydrophobic phase or composition. The surface-treated interference pigments of the present invention may have a coating comprising from about 0.1% to about 20%, alternatively from about 0.1% to about 10%, and alternatively from about 0.1% to about 3% of the total particulate weight. Nonlimiting examples of surface treatments useful herein include silicones, acrylate silicone copolymers, acrylate polymers, alkyl silane, isopropyl titanium tri-isostearate, sodium stearate, magnesium myristate, perfluoroalcohol phosphate, perfluoropolymethyl isopropyl ether, lecithin, carnauba wax, polyethylene, chitosan, lauroyl lysine, plant lipid extracts and mixtures thereof, preferably, silicones, silanes, stearates and mixtures thereof. Non-limiting examples of suitable surface-treated interference pigments include those which are silane-treated, e.g. KTZ Interval™ 11S2 series, isopropyl titanium triisostearate (ITT)-treated, e.g. KTZ Interval™ I2 series, isopropyl titanium triiosstearate/triethoxycaprylylsilane crosspolymer (TTS)-treated, e.g. KTZ Interval™ TTS2 series, and isopropyl titanium triisostearate/dimethicone crosspolymer (TTB)-treated, e.g. KTZ Interval TTB2 series, all of Kobo Products.

In one embodiment, the composition of the present invention comprises a plurality of interference pigments, wherein said plurality comprises at least one pair of (i.e. two), interference pigments. The pair comprises a first interference pigment which reflects a first reflected color, and a second interference pigment which reflects a second, complementary color. In one embodiment, the ratio of the percentage of first interference pigment to the percentage of the second interference pigment is from about 3:7 to about 7:3, alternatively from about 2:3 to about 3:2, and alternatively is about 1:1.

Alternatively, the composition of the present invention may comprise additional pairs of complementary interference pigments. When the composition comprises more than one pair of complementary interference pigments, the ratio of the percentage of one pair of complementary interference pigments to one or more additional pairs of complementary interference pigments may vary widely, for example from about 1:100 to about 100:1, provided the total amount of interference pigments is from about 0.1% to about 10%. The ratio of the first interference pigment to the second, complementary interference pigment within the individual pair may be from about 3:7 to 7:3. In one embodiment, the pairs of interference pigments are present in substantially equal amounts. Alternatively, the composition comprises two pair of complementary interference pigments wherein the ratio of the individual interference pigments is about 1:1:1:1. Examples of suitable pairs of complementary interference pigments include red with green and blue with gold.

Figure 2:
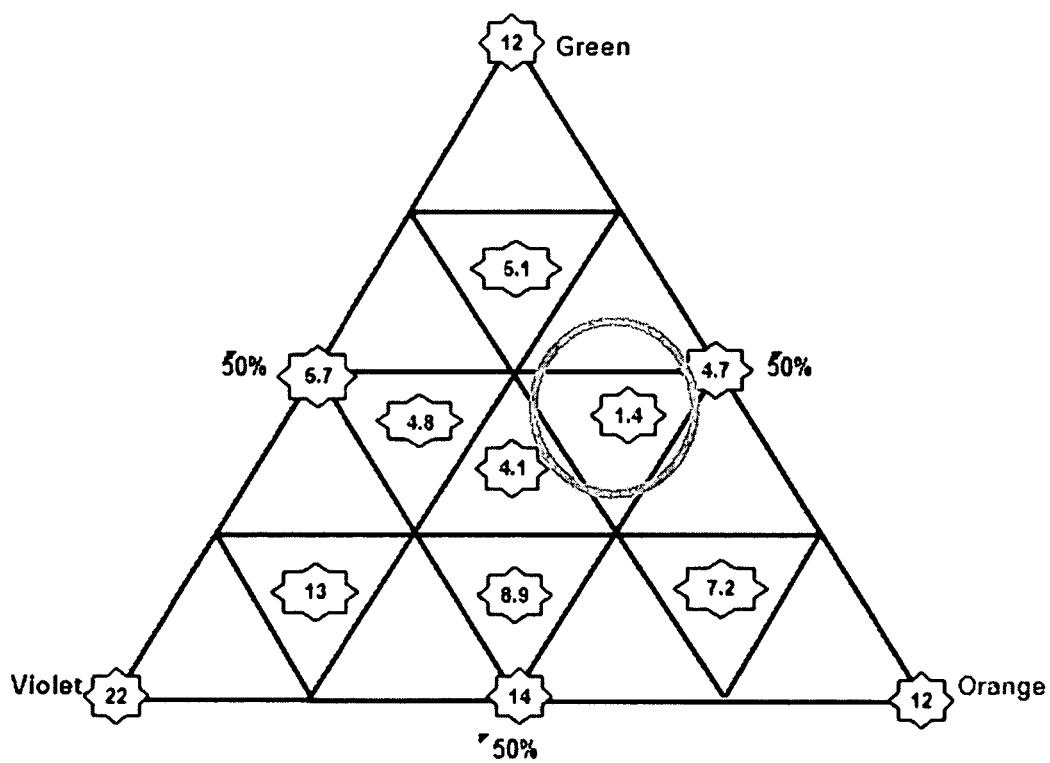
FIG. 2 depicts a three-dimensional representation of the chroma of individual compositions comprising varying percentages of orange, green and violet interference pigments, drawn on a black surface.

The composition of the present invention may comprise a plurality of interference pigments, said plurality comprising at least a first interference pigment reflecting a first color, a second interference pigment reflecting a second color, and a third interference pigment reflecting a third color. The chroma of the composition drawn on a black surface may be from about 0 to about 6, and alternatively from about 0 to about 3. Alternatively, the chroma falls within a chroma radius of about 6 units from a local minimum chroma value. In one non-limiting embodiment, the interference pigments comprise orange, green and violet interference pigments. Alternatively, the ratio of orange to green to violet interference pigments is about 5:5:2. Alternatively, the chroma falls within the circle depicted in FIG. 2 bounded by the ratio of orange to green to violet interference pigments of about 1:1:1, 10:10:1, 5:12:3 and 10:7:3. These ratios are depicted in FIG. 2, wherein the individual axes, or sides of the triangle, represent the percentage of the three pigments. The numbers in the star-shaped areas represent the chroma of the individual compositions comprising the three pigments drawn on a black surface. The area within the circle represents a local chroma minimum bounded approximately by the ratios of orange to green to violet interference pigments of about 1:1:1, 10:10:1, 5:12:3 and 10:7:3. The total amount of all interference pigments is about 2%. It is noted that a similar graph comprising chroma minima could be obtained by measuring compositions comprising other combinations of interference pigments.

The composition of the present invention may comprise a total amount of interference pigments of from about 0.1% to about 10%, alternatively from about 0.2% to about 5%, and alternatively from about 0.5% to about 3%.

The bulk compositions comprising interference pigments are substantially colorless in the absence of dyes, pigments and other colorants. In one embodiment, the bulk composition of the present invention may have a chroma of from about 0 to about 20, alternatively from about 0 to about 10, and alternatively from about 0 to about 6. Additionally or alternatively, the composition of the present invention may have a chroma of from about 0 to about 6, alternatively from about 0 to about 3, when drawn on a black surface. Additionally or alternatively, the composition of the present invention may have an adjusted contrast ratio of from about 0 to about 35, alternatively from about 0 to about 20, and alternatively from about 0 to about 12.

II. Carrier

The skin care composition of the present invention may comprise from about 50% to about 99.9% of a dermatologically acceptable carrier. The dermatologically acceptable carrier can be in a wide variety of forms, non-limiting examples of which include simple solutions (water-based or oil-based), solid forms (for example, gels or sticks), foams, mousses and emulsions. Herein, "emulsions" generally contain an aqueous phase and an oil phase. The oils may be derived from animals, plants, or petroleum, may be natural or synthetic, and may include silicone oils. Emulsion carriers include, but are not limited to, oil-in-water, water-in-oil, water-in-oil-in-water, and oil-in-water-in-silicone emulsions. In one embodiment, the dermatologically acceptable carrier comprises oil-in-water emulsions and water-in-oil emulsions. In yet another embodiment, the dermatologically acceptable carrier is an oil-in-water emulsion.

A. Emulsion

The carrier of the present invention may be in the form of an emulsion. Emulsions may contain a humectant, for example, glycerin. Emulsions may further contain an emulsifier. Emulsifiers may be nonionic, anionic or cationic. Suitable emulsifiers are disclosed in, for example, U.S. Pat. No. 3,755,560 issued to Dickert et al., U.S. Pat. No. 4,421,769, issued to Dixon et al., and *McCutcheon's Detergents and Emulsifiers*, North American Edition, pages 317-324 (1986). Suitable emulsions may have a wide range of viscosities, depending on the desired product form.

B. Actives

The composition of the present invention may comprise at least one additional skin care active, useful for improving the appearance and condition of mammalian skin and for providing long-term, or chronic, benefits. Classes of suitable skin care actives include, but are not limited to vitamins, peptides and peptide derivatives, sugar amines, sunscreens, oil control agents, flavonoid compounds, antioxidants, preservatives, phytosterols, protease inhibitors, tyrosinase inhibitors, anti-inflammatory agents, and mixtures thereof. It should be noted, however, that many skin care actives may provide more than one benefit, or operate via more than one mode of action. Therefore, classifications herein are made for the sake of convenience and are not intended to limit the active to that particular application or applications listed.

1. Vitamins

The composition of the present invention may comprise one or more vitamins, for example, to provide antioxidant and/or other nutritional benefits to the skin. Herein, "vitamins" means vitamins, pro-vitamins, and their salts, isomers and derivatives. The vitamins may include water soluble vitamins, for example, vitamin B compounds (including B3 compounds such as niacinamide; nicotinic acid, C1-C18 nicotinic acid esters, and nicotinyl alcohol; B6 compounds, such as pyroxidine; and B5 compounds, such as panthenol, or "pro-B5"); and vitamin C compounds, including ascorbyl esters of fatty acids, and ascorbic acid derivatives, for example, ascorbyl glucoside, magnesium ascorbyl phosphate, sodium ascorbyl phosphate, and ascorbyl sorbate; and mixtures thereof. The vitamins also may include those exhibiting limited solubility in water, such as vitamin A compounds, and all natural and/or synthetic analogs of Vitamin A, including retinoids, carotenoids, and other compounds which possess the biological activity of Vitamin A; vitamin D compounds; vitamin E compounds, or tocopherol, including tocopherol sorbate, tocopherol acetate, other esters of tocopherol; vitamin K compounds; and mixtures thereof. In one embodiment, the compositions of the instant invention may comprise from about 0.0001% to about 10%, alternatively from about 0.001% to about 8%, alternatively from about 0.01% to about 5%, and alternatively from about 0.1% to about 1%, of the vitamin.

2. Peptides and Peptide Derivatives

The composition of the present invention may comprise one or more peptides, for example, to aid in repair of skin, to aid in exfoliation, and to deliver other benefits to the skin. Herein, "peptide" refers to peptides containing ten or fewer amino acids, their derivatives, isomers, and complexes with other species such as metal ions (for example, copper, zinc, manganese, and magnesium). As used herein, peptide refers to both naturally occurring and synthesized peptides. In one embodiment, the peptides are di-, tri-, tetra-, penta-, and hexa-peptides, their salts, isomers, derivatives, and mixtures thereof. Examples of useful peptide derivatives include, but are not limited to, peptides derived from soy proteins, palmitoyl-lysine-threonine (pal-KT) and palmitoyl-lysine-threonine-threonine-lysine-serine (pal-KTTKS, available in a composition known as MATRIXYL®), palmitoyl-glycine-glutamine-proline-arginine (pal-GQPR, available in a composition known as RIGIN®), these three being available from Sederma, France, and Cu-histidine-glycine-glycine (Cu-HGG, also known as IAMIN®).

The composition may comprise from about $1\times10^{-7}$% to about 20%, alternatively from about $1\times10^{-6}$% to about 10%, and alternatively from about $1\times10^{-5}$% to about 5% of the peptide.

3. Sugar Amines

The composition of the present invention may comprise a sugar amine, also known as amino sugars, and their salts, isomers, tautomers and derivatives. Sugar amines can be synthetic or natural in origin and can be used as pure compounds or as mixtures of compounds (e.g., extracts from natural sources or mixtures of synthetic materials). For example, glucosamine is generally found in many shellfish and can also be derived from fungal sources. Sugar amine compounds useful in the present invention include, for example, N-acetyl-D-glucosamine, and also those described in PCT Publication WO 02/076423 and U.S. Pat. No. 6,159,485, issued to Yu, et al. In one embodiment, the composition comprises from about 0.01% to about 15%, alternatively from about 0.1% to about 10%, and alternatively from about 0.5% to about 5%, of the sugar amine.

4. Sunscreens

The composition of the present invention may comprise one or more sunscreen actives (or sunscreen agents) and/or ultraviolet light absorbers, and may be organic or inorganic. Examples of suitable sunscreen actives and ultraviolet light absorbers are disclosed in The Cosmetic, Toiletry, and Fragrance Association's *The International Cosmetic Ingredient Dictionary and Handbook*, 10$^{th}$ Ed., Gottschalck, T. E. and McEwen, Jr., Eds. (2004), p. 2267 and pp. 2292-93. Particularly suitable sunscreen actives include benzophenone, benzophenone-1, benzophenone-2, benzophenone-3, benzophenone-4, benzophenone-5, benzophenone-6, benzophenone-7, benzophenone-8, benzophenone-9, benzophenone-10, benzophenone-11, benzophenone-12, benzotriazolyl dodecyl p-cresol, 3-benzylidene camphor, benzylidene camphor sulfonic acid, benzyl salicylate, bis-ethylhexyloxyphenol methoxyphenyl triazine, bornelone, bumetrizole, butyl methoxydibenzoyl-methane, butyl PABA (p-aminobenzoic acid), cinnamidopropyl-trimonium chloride, cinoxate, dea-methoxycinnamate, dibenzoxazoyl naphthalene, di-t-butyl hydroxy-benzylidene camphor, diethylamino hydroxy-benzoyl hexyl benzoate, diethylhexyl butamido triazone, diethylhexyl 2,6-naphthalate, diisopropyl ethyl cinnamate, diisopropyl methyl cinnamate, di-methoxycinnamido-propyl ethyldimonium chloride ether, dimethyl PABA ethyl cetearyldimonium tosylate, dimorpholino-pyridazinone, dimorpholino-pyridazinone, disodium bisethylphenyl triaminotriazine stilbenedisulfonate, disodium distyrylbiphenyl disulfonate, disodium phenyl dibenzimidazole tetrasulfonate, drometrizole, drometrizole trisiloxane, ethyl dihydroxypropyl PABA, ethyl diisopropyl-cinnamate, ethylhexyl bis-isopentylbenzoxazolylphenyl melamine, ethyl dimethoxybenz-ylidene dioxoimidazolidine propionate, ethylhexyl dimethyl PABA, ethylhexyl methoxy-cinnamate, ethylhexyl methoxydibenzoyl-methane, ethylhexyl salicylate, ethylhexyl triazone, ethyl methoxycinnamate, ethyl PABA, ethyl urocanate, etocrylene, 4-(2-beta-glucopyranosiloxy) propoxy-2-hydroxybenzophenone, glyceryl ethylhexanoate dimethoxycinnamate, glyceryl PABA, glycol salicylate, hexanediol disalicylate, homosalate, isoamyl cinnamate, isoamyl p-methoxycinnamate, isopentyl trimethoxy-cinnamate trisiloxane, isopropylbenzyl salicylate, isopropyl dibenzoylmethane, isopropyl methoxy-cinnamate, kaempferia galanga root extract, menthyl anthranilate, menthyl salicylate, methoxycinnamido-propyl hydroxysultaine, methoxycinnamido-propyl laurdimonium tosylate, 4-methylbenzylidene camphor, methylene bis-benzotriazolyl tetramethylbutyl-phenol, octocrylene, octrizole, PABA, PEG-25 PABA, phenylbenzimidazole sulfonic acid, polyacrylamidomethyl benzylidene camphor, polyamide-2, polyquaternium-59, polysilicone-15, potassium methoxycinnamate, potassium phenyl-benzimidazole sulfonate, red petrolatum, sodium benzotriazoyl butylphenol sulfonate, sodium phenylbenz-imidazole sulfonate, sodium urocanate, TEA-phenylbenzimid-azole sulfonate, TEA-salicylate, terephthalylidene dicamphor sulfonic acid, tetrabutyl phenyl hydroxybenzoate, titanium dioxide, urocanic acid, zinc cerium oxide, zinc oxide, and mixtures thereof.

In one embodiment, the composition may comprise from about 1% to about 30%, and alternatively from about 2% to about 20% by weight of the composition, of the sunscreen active and/or ultraviolet light absorber. Exact amounts will vary depending upon the chosen sunscreen active and/or ultraviolet light absorber and the desired Sun Protection Factor (SPF) and spectrum of protection (e.g. UV-A and/or UV-B), and are within the knowledge and judgment of one of skill in the art.

5. Oil control agents

The composition of the present invention may comprise one or more compounds useful for regulating the production of skin oil, or sebum, and for improving the appearance of oily skin. Examples of suitable oil control agents include salicylic acid, dehydroacetic acid, benzoyl peroxide, vitamin B3 compounds (for example, niacinamide), their isomers, esters, salts and derivatives, and mixtures thereof. The compositions may comprise from about 0.0001% to about 15%, alternatively from about 0.01% to about 10%, alternatively from about 0.1% to about 5%, and alternatively from about 0.1% to about 2%, of an oil control agent.

6. Flavonoids

The composition of the present invention may comprise a flavonoid, for example, to provide anti-oxidation benefits. The flavonoid can be synthetic materials or obtained as extracts from natural sources, which also further may be derivatized. Examples of classes of suitable flavonoids are disclosed in U.S. Pat. No. 6,235,773, issued to Bissett, and include, but are not limited to, unsubstituted flavanone, methoxy flavanones, unsubstituted chalcone, 2',4-dihydroxy chalcone, and mixtures thereof. In one embodiment, the flavonoids are unsubstituted flavanones, unsubstituted chalcone (especially the trans-isomer), their glucosyl derivatives, and mixtures thereof. Other examples of suitable flavonoids include flavanones such as hesperidin and glucosyl hesperidin, isoflavones such as soy isoflavones, including but not limited to genistein, daidzein, and equol, their glucosyl derivatives, and mixtures thereof.

The composition of the present invention may comprise from about 0.01% to about 20%, alternatively from about 0.1% to about 10%, and alternatively from about 0.1% to about 5% of flavonoids.

7. Other Skin Care Actives

The composition of the present invention may comprise non-vitamin antioxidants, preservatives, phytosterols and/or plant hormones, protease inhibitors, tyrosinase inhibitors, anti-inflammatory agents and N-acyl amino acid compounds.

Suitable non-vitamin antioxidants include, but are not limited to, BHT (butylated hydroxy toluene), L-ergothioneine (available as THIOTANE™); tetrahydrocurcumin, cetyl pyridinium chloride, carnosine, diethylhexyl syrinylidene malonate (available as OXYNEX™), ubiquinone (co-enzyme Q10), and combinations thereof.

Suitable examples of plant sterols and/or plant hormones include, but are not limited to, sitosterol, stigmasterol, campesterol, brassicasterol, kinetin, zeatin, and mixtures thereof.

Suitable protease inhibitors include, but are not limited to, hexamidine, vanillin acetate, menthyl anthranilate, and mixtures thereof.

Suitable tyrosinase inhibitors include, but are not limited to, sinablanca (mustard seed extract), tetrahydrocurcumin, cetyl pyridinium chloride, and mixtures thereof.

Suitable anti-inflammatory agents include, but are not limited to, glycyrrhizic acid (also known as glycyrrhizin, glycyrrhixinic acid, and glycyrrhetinic acid glycoside), glycyrrhetenic acid, and combinations thereof.

Suitable N-acyl amino acid compounds include, but are not limited to, N-acyl phenylalanine, N-acyl tyrosine, their isomers, including their D and L isomers, salts, derivatives, and mixtures thereof. An example of a suitable N-acyl amino acid is N-undecylenoyl-L-phenylalanine is commercially available under the tradename SEPIWHITE® from Seppic (France).

Other useful skin care actives include dehydroepiandrosterone (DHEA), its analogs and derivatives; alpha- and beta-hydroxyacids, including glycolic acid and octanoyl salicylate, arbutin, dimethyl aminoethanol (DMAE), kojic acid, dihydroxy acetone (DHA), soy proteins and peptides (for example, protease inhibitors such as soybean trypsin inhibitor, and Bowman-Birk inhibitor), arbutin, their isomers, salts, and derivatives, and mixtures thereof.

III. Optional Ingredients

A. Other Particulate Materials

The composition of the present invention may comprise from about 0.1% to about 20%, alternatively from about 0.2% to about 10%, and alternatively from about 0.5% to about 5%, of particulate materials. The particulate materials can be derived from inorganic, organic, natural, and synthetic sources, and may be surface-treated. Non-limiting examples of suitable materials include almond meal, alumina, aluminum oxide, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fuller's earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, TEFLON® (i.e. polytetrafluoroethylene), polyhalogenated olefins, pumice rice bran, rye flour, sericite, silica, silk, sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are particles made from mixed polymers (e.g., copolymers, terpolymers, etc.), among such are polyethylene/polypropylene copolymer, polyethylene/propylene/isobutylene copolymer, polyethylene/styrene copolymer, and mixtures thereof. The polymeric and mixed polymeric particles may be treated via an oxidation process to destroy, for example, impurities. The polymeric and mixed polymeric particles can also optionally be cross linked with a variety of common crosslinking agents, non-limiting examples including butadiene, divinyl benzene, methylenebisacrylamide, allyl ethers of sucrose, allyl ethers of pentaerythritol, and mixtures thereof. Other examples of useful particles include waxes and resins such as paraffins, carnuba wax, ozekerite wax, candellila wax, and urea-formaldehyde resins. When such waxes and resins are used herein it is important that these materials are solids at ambient and skin temperatures.

B. Conditioning Agents

The composition of the present invention may comprise from about 0.1% to about 50%, alternatively from about 0.5% to about 30%, alternatively from about 1% to about 20%, alternatively from about 2% to 15%, of a conditioning agent. These conditioning agents include, but are not limited to, hydrocarbon oils and waxes, silicones, fatty alcohol and fatty acid derivatives, cholesterol, cholesterol derivatives, diglycerides, triglycerides, vegetable oils, vegetable oil derivatives, acetoglyceride esters, alkyl esters, alkenyl esters, lanolin, wax esters, beeswax derivatives, sterols and phospholipids, salts, isomers and derivatives thereof, and combinations thereof.

Non-limiting examples of hydrocarbon oils and waxes suitable for use herein include petrolatum, mineral oil, microcrystalline waxes, polyalkenes, paraffins, cerasin, ozokerite, polyethylene, perhydrosqualene, poly alpha olefins, hydrogenated polyisobutenes and combinations thereof.

Non-limiting examples of silicone oils suitable for use herein include dimethicone copolyol, silicone cross-polymers, dimethylpolysiloxane, diethylpolysiloxane, mixed $C_{1-30}$ alkyl polysiloxanes, phenyl dimethicone, dimethiconol, and combinations thereof. In one embodiment, the silicone oils are non-volatile silicone oils selected from the group consisting of dimethicone, dimethiconol, mixed $C_{1-30}$ alkyl polysiloxanes, silicone crosspolymers, and combinations thereof. These and other examples of silicone oils useful herein are described in U.S. Pat. No. 5,011,681, issued to Ciotti et al.

Non-limiting examples of silicone cross-polymers suitable for use herein include acrylate/bis-hydroxypropyl dimethicone crosspolymer, $C_{30-45}$ alkyl cetearyl dimethicone crosspolymer, acrylate/bis-hydroxypropyl dimethicone crosspolymer, $C_{30-45}$ alkyl cetearyl dimethicone crosspolymer, cetearyl dimethicone/vinyl dimethicone crosspolymer, dimethicone crosspolymer, dimethicone crosspolymer-3, dimethicone/phenyl vinyl dimethicone crosspolymer, dimethicone/vinyl dimethicone crosspolymer, diphenyl dimethicone crosspolymer, divinyldimethicone/dimethicone crosspolymer, polyethylene glycol (PEG)-10 dimethicone crosspolymer, PEG-12 dimethicone crosspolymer, PEG-10 dimethicone/vinyl dimethicone crosspolymer, PEG-10/lauryl dimethicone crosspolymer, PEG-15/lauryl dimethicone crosspolymer, trifluoropropyl dimethicone/trifluoropropyl divinyldimethicone crosspolymer, vinyl dimethicone/lauryl dimethicone crosspolymer, vinyldimethyl/trimethylsiloxysilicate stearyl dimethicone crosspolymer, polysilicone-11, and mixtures thereof.

Other conditioning agents also useful herein are various $C_{1-30}$ monoesters and polyesters of sugars and related materials, for example, sucrose esters of fatty acids (SEFA), triglyceride esters acetoglyceride esters, alkyl esters of fatty acids having 10 to 20 carbon atoms, alkenyl esters of fatty acids having 10 to 20 carbon atoms, fatty acids having 10 to 20 carbon atoms, fatty alcohols having 10 to 20 carbon atoms, lanolin, polyhydric alcohol esters, wax esters, vegetable waxes, phospholipids, sterols, amides, isomers, salts, derivatives and mixtures thereof. These and other suitable conditioning agents are exemplified in U.S. Pat. No. 5,997,890, issued to Sine et al.

C. Structuring Agent

The composition of the present invention may comprise a structuring agent. Without being limited by theory, it is believed that the structuring agent assists in providing rheological characteristics (for example yield and structural characteristics) to the composition which contribute to the stability of the composition. When present, the compositions of the present invention may comprise from about 0.1% to about 20%, alternatively from about 0.5% to about 10%, and alternatively from about 1% to about 5%, of one or more structuring agents.

The structuring agents of the present invention may be selected from the group consisting of stearic acid, palmitic acid, stearyl alcohol, cetyl alcohol, behenyl alcohol, palmitic acid, the polyethylene glycol ether of stearyl alcohol having an average of from about 1 to about 5 ethylene oxide units, the polyethylene glycol ether of cetyl alcohol having an average of from about 1 to about 5 ethylene oxide units, and mixtures thereof. In one embodiment, structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. In another embodiment, structuring agents are selected from the group consisting of stearic acid, palmitic acid, stearyl alcohol, cetyl alcohol, behenyl alcohol, steareth-2, and mixtures thereof.

D. Thickening Agent

The composition of the present invention may comprise from about 0.1% to about 5%, alternatively from about 0.1% to about 4%, and alternatively from about 0.25% to about 3%, of one or more thickening agents, including thickeners and gelling agents. Nonlimiting classes of thickening agents include crosslinked polyacrylate polymers and copolymers, polyacrylamide polymers and copolymers, polyacryloyldimethyl taurates, aminomethylpropanol (AMP)-based copolymers, polysaccharides and gums. In one embodiment, compositions of the present invention include a thickening agent selected from carboxylic acid polymers, crosslinked polyacrylate polymers, polyacrylamide polymers, and mixtures thereof. In yet another embodiment, the thickening agent is selected from carboxylic acid polymers, polyacrylamide polymers, and mixtures thereof.

E. Substrates

The compositions of the present invention can be applied directly to the skin. Additionally or alternatively, the compositions can be releasably applied to a substrate material and subsequently applied to the skin. In one embodiment, the composition is pre-combined with or deposited onto the substrate to form a wipe product, one non-limiting example of which includes disposable wipe products. Herein, "wipe product" means a substrate and a composition of the present invention which are pre-combined for later use. Wipe products may be packaged in a relatively dry state and wetted prior to use, or may be packaged having already been wetted. The compositions and wipe products are well-suited for use in treating the skin and hair, however may also be useful in other applications.

Suitable wipe substrates include, but are not limited to, nonwovens, films, foams, sponges, and combinations thereof. In one embodiment, wipe substrates comprise a porous material which is capable of holding the composition within the pores of the substrate. In one embodiment, the substrate is nonwoven.

Techniques for combining wipe substrates with a cleansing or treating composition, and for their packaging, are well known in the art and are applicable to the present invention. In general, the wipe substrate is combined with the composition by one or more techniques involving coating, immersing, dipping, spraying, extruding. In general, the wipes are combined with an amount of the composition sufficient to provide effective skin application.

IV. Method

The present invention provides for a method for improving visible discontinuities in mammalian skin and for improving the condition of mammalian skin. The present invention further provides a method for improving the appearance of hyperchromic and/or hyperpigmentes portions of skin. All methods comprise the step of topically applying to the skin an effective amount of a skin care composition of the present invention. Any part of the external portion of the skin can be treated. The amount of the composition applied, the frequency of application and the period of use will vary widely depending upon the level of components of a given composition and the level of improvement desired. In one embodiment, the compositions are applied at least once daily, where "daily" and "days" mean a 24-hour period. For example, the compositions may be applied daily for 30 consecutive days, alternatively for 14 consecutive days, alternatively for 7 consecutive days and alternatively for one day.

The application of the present compositions may be done using the palms of the hands, the fingers, or by using an implement (e.g., a cotton ball, swab, pad, etc.). The compositions may be releasably applied to a carrier substrate, suitable for use at a later time. The compositions further may be used in combination with a delivery enhancement device, non-limiting examples of which include an implement, such as a sponge or sponge-tipped applicator, a spray applicator, a brush, and combinations thereof.

V. Kit

The present invention further may comprise a kit, said kit comprising a skin care composition as described herein. The kit further may comprise one or more additional compositions, instructions for applying the composition(s), instructions for complying with a suitable application regimen, an implement, a substrate, a delivery enhancement device, a dietary supplement, and combinations thereof. The kit may comprise an outer packaging unit, which in turn may comprise one or more smaller, inner packaging units.

The inner packaging units may comprise one or more of the individual components of the kit. The inner and outer packaging units may be of any type suitable for containing, presenting and/or reasonably protecting from damage the contents of the kit. The inner packaging units each may contain a quantity of a composition suitable for use in a single application regimen. In one example, the individual packaging units each will contain 10 ml, alternatively 5 ml, alternatively 2 ml, and alternatively 1 ml of a composition described herein.

VI. EXAMPLES

Examples 1-5

A Moisturizing Lotion/Cream May be Prepared by the Method Described Herein from the Following Components

|  | Example 1 | Example 2 | Example 3 | Example 4 | Example 5 |
|---|---|---|---|---|---|
| Water Phase: | | | | | |
| Water | qs | qs | qs | qs | qs |
| Glycerin | 3.0 | 5.0 | 7.0 | 10.0 | 15.0 |
| Disodium EDTA | 0.1 | 0.1 | 0.05 | 0.1 | 0.1 |
| Methylparaben | 0.1 | 0.1 | 0.1 | 0.1 | 0.1 |
| Niacinamide | 2.0 | 0.5 | 3.5 | 3.0 | 5.0 |
| D-panthenol | 0.5 | 0.1 | 1.0 | 0.5 | 1.5 |
| Sodium Hydroxide | 0.001 | 0.002 | 0.001 | 0.001 | 0.001 |
| Benzyl alcohol | 0.25 | 0.25 | 0.25 | 0.25 | 0.25 |
| FD&C Red #40 | — | — | — | — | — |
| Hexamidine isethionate | 0.01 | — | — | — | — |
| Palmitoylpentapeptide[1] | 0.0002 | — | — | — | 0.0003 |
| N-acetyl glucosamine | 2.0 | — | 2.0 | — | 5.0 |
| Oil Phase: | | | | | |
| Isohexadecane | 3.0 | 3.0 | 3.0 | 4.0 | 3.0 |
| Isopropyl Isostearate | 1.0 | 0.5 | 1.3 | 1.5 | 1.3 |
| Sucrose polyester | 0.7 | — | 0.7 | 1.0 | 0.7 |
| Octinoxate | — | — | — | — | 4.0 |
| Avobenzone | — | — | — | — | 0.5 |
| Phytosterol | — | — | — | 0.1 | — |
| Cetyl alcohol | 0.4 | 0.3 | 0.4 | 0.5 | 0.4 |
| Stearyl alcohol | 0.5 | 0.35 | 0.5 | 0.6 | 0.5 |
| Behenyl alcohol | 0.4 | 0.3 | 0.4 | 0.5 | 0.4 |
| PEG-100 stearate | 0.1 | 0.1 | 0.1 | 0.2 | 0.1 |
| Stearic Acid | 0.1 | 0.05 | 0.1 | 0.2 | 0.1 |
| Cetearyl glucoside | 0.1 | 0.1 | 0.1 | 0.25 | 0.1 |
| Thickener: | | | | | |
| Polyacrylamide/C13-14 isoparaffin/laureth-7 | 1.5 | — | 2.0 | 2.5 | 2.0 |
| Sodium acrylate/sodium acryloyldimethyl taurate copolymer/isohexadecane/polysorbate 80 | — | 3.0 | — | — | — |
| Interference Pigments: | | | | | |
| KTZ Interfine ™ Blue[2] | 2.5 | — | — | — | 0.5 |
| KTZ Interfine ™ Gold[2] | 2.5 | — | 0.3 | — | 0.5 |
| KTZ Interfine ™ Red[2] | — | 1.0 | — | — | 0.5 |
| KTZ Interfine ™ Green[2] | — | 1.0 | — | 0.83 | 0.5 |
| KTZ Interfine ™ Violet[2] | — | — | 0.3 | 0.34 | — |
| Prestige Silk ™ Orange[3] | — | — | — | 0.83 | — |
| Additional Ingredients: | | | | | |
| Dimethicone/dimethiconol | — | 1.0 | 2.0 | 0.5 | 2.0 |
| Fragrance | — | 0.1 | 0.1 | 0.1 | 0.1 |
| Polymethylsilsequioxane | — | — | 0.25 | — | 1.0 |
| Nylon-12 | — | 0.5 | — | — | — |
| Total: | 100% | 100% | 100% | 100% | 100% |

[1]Palmitoyl-lysine-threonine-threonine-lysine-serine available from Sederma (France)
[2]Titanium dioxide coated mica available from Kobo Products Inc.
[3]Titanium dioxide and tin oxide coated mica available from Eckart In a suitable vessel, combine the water phase ingredients and heat to 75° C. In a separate suitable vessel, combine the oil phase ingredients and heat to 75° C. Add the oil phase to the water phase and mill the resulting emulsion (e.g., with a TEKMAR™ T-25). Add the thickener to the emulsion and cool to 45° C. while stirring. At 45° C., add the interference pigments and remaining ingredients. Cool the product with stirring to 30° C. and pour into suitable containers.

Examples 6-10

A Moisturizing Serum/Lotion May be Prepared by the Method Described Herein from the Following Components

|  | Example 6 | Example 7 | Example 8 | Example 9 | Example 10 |
|---|---|---|---|---|---|
| Water Phase: | | | | | |
| Water | qs | qs | qs | qs | qs |
| Glycerin | 3.0 | 5.0 | 7.0 | 10.0 | 15.0 |
| Disodium EDTA | 0.1 | 0.1 | 0.05 | 0.1 | 0.1 |
| Niacinamide | 2.0 | 0.5 | 3.5 | 3.0 | 5.0 |
| D-panthenol | 0.5 | 0.1 | 1.0 | 0.5 | 1.5 |
| FD&C Red #40 | — | — | 0.0002 | — | — |
| FD&C Yellow #10 | — | — | — | — | 0.0004 |
| Palmitoylpentapeptide[1] | 0.0002 | — | — | — | 0.0003 |
| N-acetyl glucosamine | 2.0 | — | 2.0 | — | 5.0 |
| Silicone/Oil Phase: | | | | | |
| Cyclomethicone D5 | 10.0 | 5.0 | 5.0 | 10.0 | 7.5 |
| Dow Corning ® 9040 silicone elastomer[2] | — | 10.0 | 5.0 | 5.0 | 7.5 |
| KSG-15AP silicone Elastomer[3] | 5.0 | — | 5.0 | 5.0 | 7.5 |
| Dimethione/dimethiconol | — | 2.0 | 2.0 | 1.0 | 2.0 |
| Dimethicone 50 csk | 1.0 | — | — | — | — |
| Vitamin E Acetate | — | 0.5 | — | 0.1 | — |
| Thickener: | | | | | |
| Polyacrylamide/C13-14 isoparaffin/laureth-7 | 2.5 | 2.5 | 3.0 | — | — |
| Sodium acrylate/sodium acryloyldimethyl taurate copolymer/isohexadecane/polysorbate 80 | — | — | — | 3.0 | — |
| Acrylates/C10-30 alkyl acrylates crosspolymer | — | — | — | — | 0.5 |
| Interference Pigments: | | | | | |
| Timiron Splendid ™ Gold[4] | 1 | 0.4 | — | — | — |
| Timiron Splendid ™ Blue[4] | 1.2 | 0.35 | — | — | — |
| KTZ Interval ™ Red[5] | — | 0.4 | — | 1.0 | 0.9 |
| KTZ Interval ™ Green[5] | — | 0.35 | — | 1.0 | 0.8 |
| Prestige Silk ™ Blue[6] | — | — | 1.5 | — | — |
| Prestige Silk ™ Gold[6] | — | — | 1.5 | — | — |
| Cosmica ™ Orange[7] | — | — | — | 0.1 | — |
| Additional Ingredients: | | | | | |
| Fragrance | — | 0.1 | 0.1 | 0.1 | 0.1 |
| Triethanolamine | — | — | — | — | 0.6 |
| PTFE | — | 0.5 | — | — | — |
| Polymethylsilsequioxane | — | 0.5 | 1.0 | — | — |
| Polyethylene | — | 0.5 | — | — | 1.0 |
| Total: | 100% | 100% | 100% | 100% | 100% |

[1] Palmitoyl-lysine-threonine-threonine-lysine-serine available from Sederma (France)
[2] A silicone elastomer dispersion from Dow Corning Corp.
[3] A silicone elastomer dispersion from Shin Etsu
[4] Titanium dioxide and silica coated mica from EMD Chemicals Inc.
[5] Titanium dioxide coated mica from Kobo Products Inc.
[6] Titanium dioxide and tin oxide coated mica from Eckart.
[7] Iron oxide coated mica from Engelhard Corporation.

In a suitable vessel, combine the water phase ingredients and mix until uniform. In a separate suitable container, combine the silicone/oil phase ingredients and mix until uniform. Add half the thickener and then the silicone/oil phase to the water phase and mill the resulting emulsion (e.g., with a Tekmar™ T-25). Add the remainder of the thickener, the interference pigments, and then the remaining ingredients to the emulsion while stirring. Once the composition is uniform, pour the product into suitable containers.

Examples 11-12

A Moisturizing Cream/Lotion is Prepared by the Method Described Herein From the Following Components

| Component | Example 11 | Example 12 |
|---|---|---|
| Phase A | | |
| Water | q.s. | q.s. |
| Allantoin | 0.2 | 0.2 |
| Disodium EDTA | 0.1 | 0.1 |
| Ethyl paraben | 0.2 | 0.2 |
| Propyl paraben | 0.1 | 0.1 |
| BHT | 0.015 | 0.015 |
| Dexpanthenol | 1.0 | 0.5 |
| Glycerin | 7.5 | 10.0 |
| Niacinamide | 2.0 | 3.5 |
| Palmitoyl-pentapeptide[1] | — | 0.0003 |
| Benzyl alcohol | 0.2500 | 0.2500 |
| Green tea extract | 1.0 | 0.1 |
| N-acetyl glucosamine | 5.0 | 2.0 |
| Sodium metabisulfite | 0.1 | 0.01 |
| Phase B | | |
| Cyclopentasiloxane | 15.0000 | 15.0000 |
| C12-C15 alkyl benzoate | 1.5 | — |
| Vitamin E acetate | 0.5 | 0.1 |
| Retinyl propionate | 0.15 | — |
| Phytosterol | 0.1 | — |
| KSG-21 silicone elastomer[2] | 4.0 | 4.0 |
| Dow Corning ® 9040 silicone elastomer[2] | 15.0 | 15.0 |
| Abil ™ EM-97 dimethicone copolyol[3] | 0.5 | — |
| Polymethylsilsesquioxane | 2.5 | 0.5 |
| Fragrance | — | 0.1 |
| Phase C | | |
| KTZ Interval ™ Gold-11S2[4] | 0.75 | 0.3 |
| KTZ Interval ™ Blue-11S2[4] | 0.75 | 0.3 |
| KTZ Interval ™ Red-11S2[4] | — | 0.3 |
| KTZ Interval ™ Green-11S2[4] | — | 0.3 |

[1] Palmitoyl-lysine-threonine-threonine-lysine-serine available from Sederma (France)
[2] KSG-21 is an emulsifying silicone elastomer available from Shin Etsu
[3] A silicone elastomer dispersion from Dow Corning Corp
[4] Abil EM-97 available from Goldschmidt Chemical Corporation
[5] Silane surface treated titanium dioxide coated mica from Kobo Products Inc.

In a suitable vessel, blend the Phase A components with a suitable mixer until all of the components are dissolved. Blend Phase B components in suitable vessel and mix until uniform. Add Phase A slowly to Phase B with mixing and continue mixing until uniform. Mill the resulting product for about 5 minutes using an appropriate mill (e.g., TEKMAR™ T-25). Next, add Phase C while stirring the product. Continue mixing until the product is uniform, and pour the product into suitable containers.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin care composition comprising a plurality of interference pigments and a dermatologically acceptable carrier, wherein said plurality comprises at least a first interference pigment which reflects a first color, and at least a second interference pigment which reflects a second, complementary color, and wherein the total amount of interference pigments is from about 0.1% to about 10%;
wherein said first color is blue and said second color is gold and wherein the chroma of the bulk skin care composition is from about 0 to about 20; and wherein said composition is deposited onto a substrate to form a wipe product.

2. The composition of claim 1, wherein the ratio of the percentage of said first interference pigment to the percentage of said second interference pigment is from about 3:7 to about 7:3.

3. The composition of claim 1 wherein the chroma of said composition drawn on a black surface is from about 0 to about 10.

4. The composition of claim 1, wherein the adjusted contrast ratio of said composition is from about 0 to about 35.

5. The composition of claim 1, wherein said composition further comprises a third and a fourth interference pigment, wherein said third interference pigment reflects a third color and wherein said fourth interference reflects a fourth color complementary to the third color.

6. The composition of claim 5, wherein the ratio of the percentages of the first, the second, the third and the fourth interference pigment is about 1:1:1:1.

7. The composition of claim 1, wherein the composition additionally comprises at least one skin care active.

8. The composition of claim 7, wherein said skin care active is selected from the group consisting of vitamin B compounds, vitamin C compounds, vitamin E compounds, peptides, sunscreens, ultraviolet light absorbers, oil control agents, and combinations thereof.

9. The composition of claim 8, wherein the skin care active is selected from the group consisting of niacinamide, palmitoyl-lysine-threonine, palmitoyl-lysine-threonine-threonine-lysine-serine, N-acetyl-D-glucosamine, salicylic acid, dehydroacetic acid, sodium dehydroacetate, and combinations thereof.

10. A skin care composition comprising a plurality of interference pigments, said plurality comprising at least a first interference pigment reflecting a orange color, a second interference pigment reflecting a green color, and a third interference pigment reflecting a violet color, and a dermatologically acceptable carrier, wherein the chroma of the composition drawn on a black surface is from about 0 to about 6 and wherein the total amount of interference pigments is from about 0.1% to about 10%.

11. The composition of claim 10 wherein the chroma of the bulk composition is from about 0 to about 10.

12. The composition of claim 10, wherein the adjusted contrast ratio is from about 0 to about 35.

13. The composition of claim 10, wherein the ratio of the first to the second to the third interference pigment is about 5:5:2.

14. The composition of claim 10, wherein the composition additional comprises at least one skin care active.

* * * * *